(12) United States Patent
Morisseau

(10) Patent No.: US 8,088,137 B2
(45) Date of Patent: Jan. 3, 2012

(54) SAFETY TROCAR WITH LANCET FEATURE

(76) Inventor: Michel Morisseau, Melesse (FR)

( * ) Notice: Subject to any disclaimer, the term of this patent is extended or adjusted under 35 U.S.C. 154(b) by 598 days.

(21) Appl. No.: 11/910,473

(22) PCT Filed: Mar. 8, 2006

(86) PCT No.: PCT/US2006/008753
§ 371 (c)(1),
(2), (4) Date: Oct. 2, 2007

(87) PCT Pub. No.: WO2006/096868
PCT Pub. Date: Sep. 14, 2006

(65) Prior Publication Data
US 2008/0281344 A1     Nov. 13, 2008

Related U.S. Application Data

(60) Provisional application No. 60/659,814, filed on Mar. 8, 2005.

(51) Int. Cl.
*A61B 17/34* (2006.01)

(52) U.S. Cl. .................. 606/185; 606/182; 604/264

(58) Field of Classification Search ............... 604/164, 604/264, 272, 506, 158, 165.02; 606/158, 606/167, 170, 172, 184–185, 182
See application file for complete search history.

(56) References Cited

U.S. PATENT DOCUMENTS

| 5,320,610 A | 6/1994 | Yoon |
| 5,324,268 A | 6/1994 | Yoon |
| 5,350,393 A | 9/1994 | Yoon |
| 5,360,405 A | 11/1994 | Yoon |
| 5,411,515 A * | 5/1995 | Haber et al. ............ 606/184 |

(Continued)

FOREIGN PATENT DOCUMENTS

JP    10506558    6/1998

(Continued)

OTHER PUBLICATIONS

European Office Action for Application No. 06737885.1-2310 dated Jun. 14, 2011.

(Continued)

*Primary Examiner* — Ryan Severson
*Assistant Examiner* — Ashley Cronin
(74) *Attorney, Agent, or Firm* — Bachman & LaPointe, P.C.

(57) ABSTRACT

A trocar assembly includes a trocar housing having a blunt distal end and a proximal end; a blade assembly having a sharp tip and being slideable within the trocar housing between and armed position wherein the sharp tip extends distally beyond the blunt distal end and a relaxed position wherein the sharp tip is withdrawn proximally relative to the armed position; and a trigger member positioned relative to the housing to contact tissue when tissue is cut with the blade assembly in the armed position, and slideable by contact with the tissue to a proximal position which exposes the sharp tip and actuates a lock release member, the trigger member having member having a spring member biasing the trigger member distally so that removal of contact with the tissue allows the spring to move the trigger member distally, and further wherein distal movement of the trigger member with the lock release member activated releases the blade assembly from the armed position and allows the blade assembly to move to the relaxed position.

12 Claims, 3 Drawing Sheets

U.S. PATENT DOCUMENTS

| | | | | |
|---|---|---|---|---|
| 5,578,053 A | * | 11/1996 | Yoon | 606/185 |
| 5,676,683 A | * | 10/1997 | Yoon | 606/185 |
| 5,807,402 A | | 9/1998 | Yoon | |
| 5,916,232 A | * | 6/1999 | Hart | 606/185 |
| 5,993,470 A | | 11/1999 | Yoon | |
| 6,017,356 A | | 1/2000 | Frederick et al. | |

FOREIGN PATENT DOCUMENTS

| | | |
|---|---|---|
| WO | 9311811 | 6/1993 |
| WO | 9406681 | 3/1994 |
| WO | 9626752 | 9/1996 |

OTHER PUBLICATIONS

Japanese Office Action for Application No. 2008-500995 dated Jul. 5, 2011.

* cited by examiner

SAFETY TROCAR WITH LANCET FEATURE

BACKGROUND OF THE INVENTION

Field of the Invention

The invention relates to what is known as a "safety trocar" which, in accordance with the present invention, has enhanced safety features and also has a lancet function.

As is well known in the industry, trocars are elongated sharp objects which are particularly used for making an incision in the course of surgical procedures, especially laparascopic and endoscopic procedures.

Such devices are used to penetrate the body wall, and thereby position a canula or tube through the body wall through which surgical instruments can be introduced for performing the desired surgical or medical procedures.

A long standing problem in the industry has been to provide suitable protection to underlying tissues and organs which might be damaged by an unshielded tip of a trocar. This problem is made more serious by virtue of the fact that the body wall gives substantial resistance to being pierced by the trocar, which then has the tendency to spring forward once the incision has been completed.

Many attempts have been made to provide suitable solutions to this problem. These various different attempts are too numerous to mention here. Nevertheless, despite these various efforts, the problem remains in the industry.

Based upon the foregoing, it is the primary object of the present invention to provide a trocar which has reliable and effective shielding and protection from injury to underlying organs and tissues.

It is a further object of the present invention to provide such a trocar which has additional functionality, specifically, in the form of a lancet.

SUMMARY OF THE INVENTION

In accordance with the present invention, the foregoing objects and advantages have been readily attained.

According to the invention, a trocar is provided which has a longitudinally moveable blade and also a longitudinally moveable trigger/shield member. As will be set forth in detail in the description below, a button and triggering assembly are provided which allow for a series of different operational positions of the trocar. These include a relaxed position wherein the sharp blade member of the trocar is proximally positioned, with the sharp tip of the trocar positioned proximally of both a distal housing portion of the trocar and also the shield member. In this position, the blade cannot be exposed regardless of position of the shield, and the blade is therefore completely shielded. The blade is also positionable to an armed position, wherein the blade is positioned distally so as to position the tip of the blade beyond the blunt housing tip, but not beyond the tip of the shield member. When armed, the blade is held in this position by a releasable lock member.

The trigger/shield member is freely moveable between an extended position wherein it extends beyond the tip of the trocar blade, even in the armed position, and a rearward position wherein the blade in the armed position can be exposed. The trigger/shield member is associated with the lock mechanism so that rearward movement of the trigger/shield member engages a ratchet or other surface with the blade lock, and forward movement of the shield member disengages the blade lock and thereby provides for the blade to withdraw proximally into the housing of the trocar.

Thus, in accordance with present invention, rearward movement of the trigger member caused by contact with body tissue to be pierced, followed by forward movement of the trigger member as the trigger member forces through the opening, disengages the blade and causes the blade to be withdrawn proximally into the housing of the trocar as desired. In this way, the blade is positioned into a safe location as soon as the incision is completed.

In accordance with a further embodiment of the invention, the trigger member is never locked in a forward position, but is rather only biased toward that position. Thus, trauma and injury to underlying tissues and organs from the trigger is also prevented.

In further accordance with the invention, the blade can be manually positioned to a distal location which extends beyond the distal-most position of the shield, and in this configuration the device can be used as a lancet as desired.

The structures and positions as described above will be more thoroughly described in connection with the detailed description presented below.

BRIEF DESCRIPTION OF THE DRAWINGS

A detailed description of preferred embodiments of the present inventions follows, with reference to the attached drawings, wherein.

DETAILED DESCRIPTION

Figure 1:
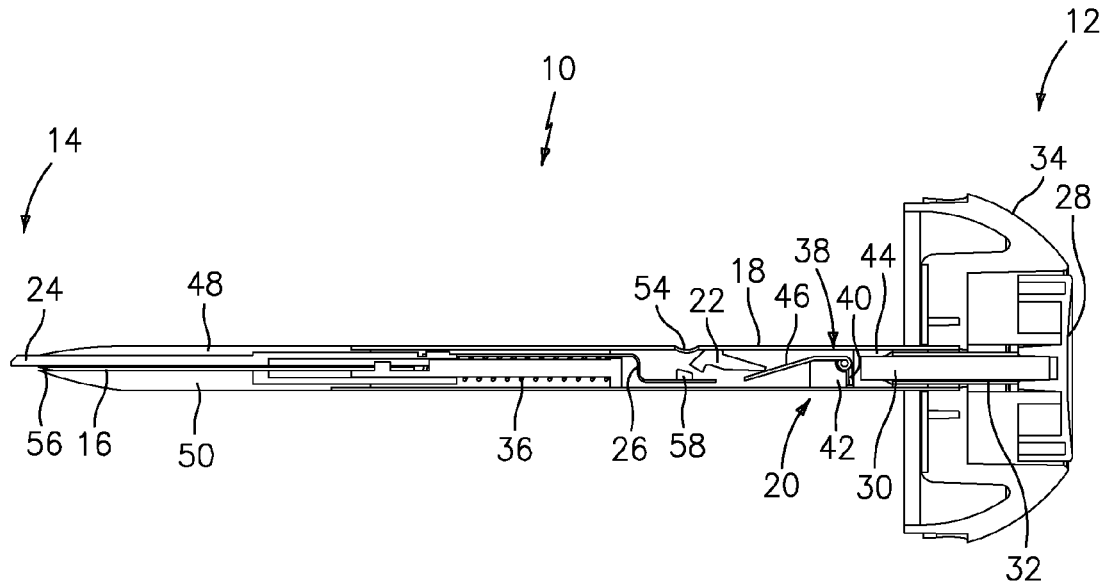
FIG. 1 shows a trocar in accordance with the present invention in a relaxed position.

The invention relates to a shielded trocar with a lancet function. The trocar advantageously allows for enhanced shielding and security of the blade, and also allows for use of the blade as a lancet which broadens the usability of the surgical instrument as will be discussed below. Referring to the drawings, a preferred embodiment is illustrated. The drawings show sectional and to some extent perspective views to illustrate the details of the invention.

FIG. 1 shows a trocar 10 having a handle 12 positioned at a generally proximal end and a tip 14 positioned at a generally distal end.

According the invention, trocar 10 includes a substantially flat blade 16 which is slidably positioned relative to a tube or housing 18. Blade 16 is mounted in a blade holder 20 which is also slidably positioned within tube 18. A blade lock member 22 is pivotably mounted to blade holder 20, and engagable in certain positions with tube 18 as will be discussed below. The entire assembly of blade 16, blade holder 20 and blade lock member 22 are advantageously slidable within tube 18 and biased toward a proximal end of the device.

In further accordance with the invention, and still referring FIG. 1, trocar 10 also advantageously includes a a substantially flat shield/trigger member 24 which is also slidably mounted within tube 18, and shield 24 is longitudinally connected to a lock release member 26. Shield 24 and lock release member 26 are advantageously biased by a spring in a distal direction relative to tube 18.

The assembly of blade 16, blade holder 20 and blade lock 22 are moveable along the axis of tube 18 between a withdrawn position wherein the sharpened tip of blade 16 is positioned within the housing, an extended locked position wherein sharp tip of blade 16 extends beyond the housing but not beyond extended shield 24, and a lancet position wherein the sharp tip of blade 16 is extended beyond the extended distal tip of shield 24.

This slidable movement is, as set forth above, dictated by influence of a spring and also by a handle button 28 which receives a connecting post 30 as well as a connecting sleeve 32 which are in contact with blade holder 20 as shown in FIG. 1.

The assembly of shield member 24 and lock release member 26 are also advantageously axially moveable within tube 18, and are biased toward a distal end of trocar 10 as discussed above. As will be discussed below, during use of trocar 10 to perform an incision, pressure is exerted upon shield 24 which causes shield 24 and lock release 26 to move proximally and allow the sharp tip of the blade in an armed position to be used for cutting.

Handle button 28 can advantageously be mounted within a proximally opening recess within a handle housing 34 for the device. Handle housing 34 can advantageously be shaped to fit comfortably within the hand of a user, and also preferably to mate with the housing of a canula (not shown) into which trocar 10 will be positioned.

FIG. 1 shows a spring 36 which advantageously can be positioned so as to exert force on blade holder 20 in a proximal direction and on shield 24 in a distal direction. This advantageously serves to bias both assemblies within tube 18 as desired.

Still further, a spring can advantageously be mounted to blade holder 20 for exerting a pivotable force on lock member 22. This can advantageously be a coiled spring 38 which can be mounted to blade holder 20 with one arm 40 positioned between a spring block 42 and the back surface of a post holder 44 of blade holder 20, and with a second arm 46 exerting a force on lock member 22.

Trocar 10 still further advantageously includes two additional distal housing members 48, 50, which support shield 24 and blade 16 respectively.

Distal housing members 48, 50 advantageously terminate in a blunt and rounded tip which is specifically designed and adapted to provide little or no risk of trauma or injury to any tissue which might contact same. Distal housing members 48, 50 advantageously mount with or are otherwise connected to tube 18 and distal housing members 48, 50 and tube 18 define the housing component of trocar 10 in accordance with the present invention.

FIGS. 2-5 illustrate the trocar of FIG. 1 with the components in various different positions.

Figure 2:
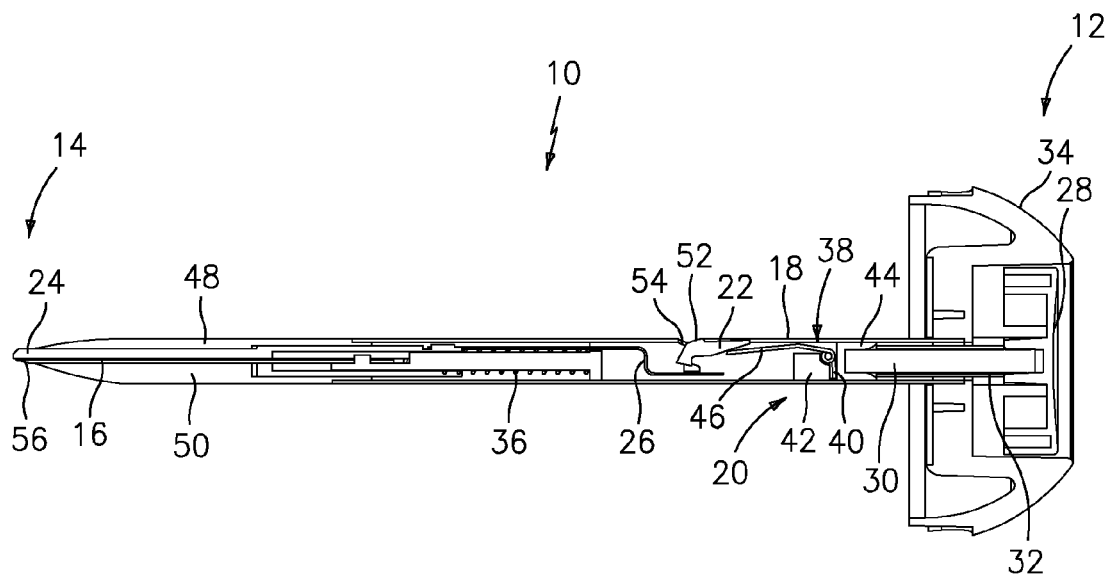
FIG. 2 shows a trocar in accordance with the present invention in an armed position.

Specifically, FIG. 2 shows trocar 10 with blade 16, blade holder 20 and blade lock 22 locked in a distal armed position. In this position, lock 22 has a catch member 52 which is advantageously engaged against proximal movement, in this instance by extending into an opening or hole 54 in tube 18. In this position, the sharp tip 56 of blade 16 extends beyond distal housing 48, 50, but is still overlapped by shield member 24 as shown. Trocar 10 is positioned in this configuration by depressing button 28 sufficiently that lock 52 engages with the opening 54 in tube 18, and this engagement is advantageously visible from exterior of tube 18 so that a user can readily know whether trocar 10 is armed.

Figure 3:
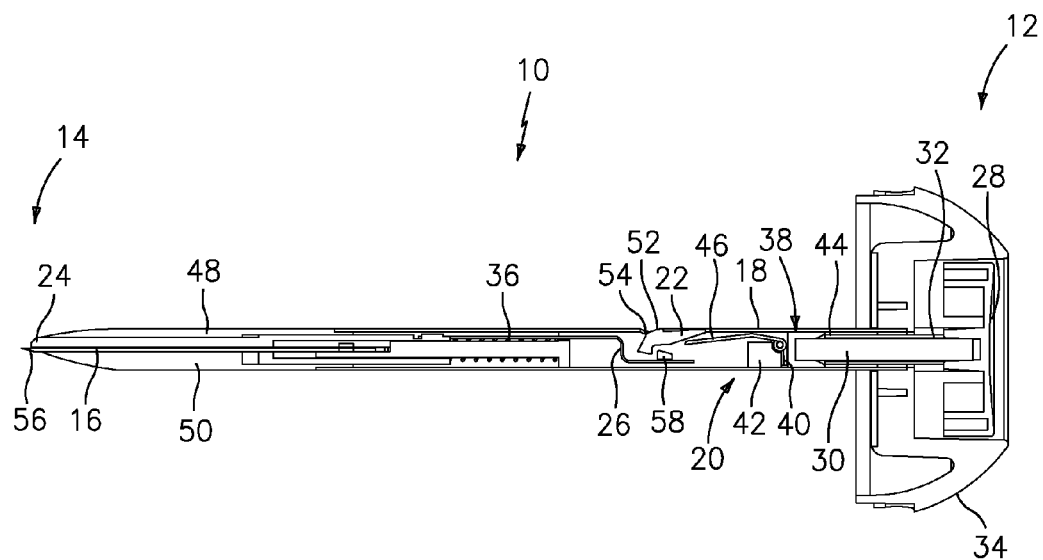
FIG. 3 shows a trocar in accordance with the present invention with the blade and shield in a cutting position.

FIG. 3 shows the trocar in a position which would be accomplished during a cutting procedure. During such a procedure, shield 24 is pushed proximally against the bias of spring 36 so as to expose sharp tip 56 which pierces and penetrates the tissue as desired. The proximal movement of shield 24 also proximally moves lock release member 26 so as to engage a tooth 58 of lock release member 26 behind a portion of blade lock 22 as shown in FIG. 3.

Figure 4:
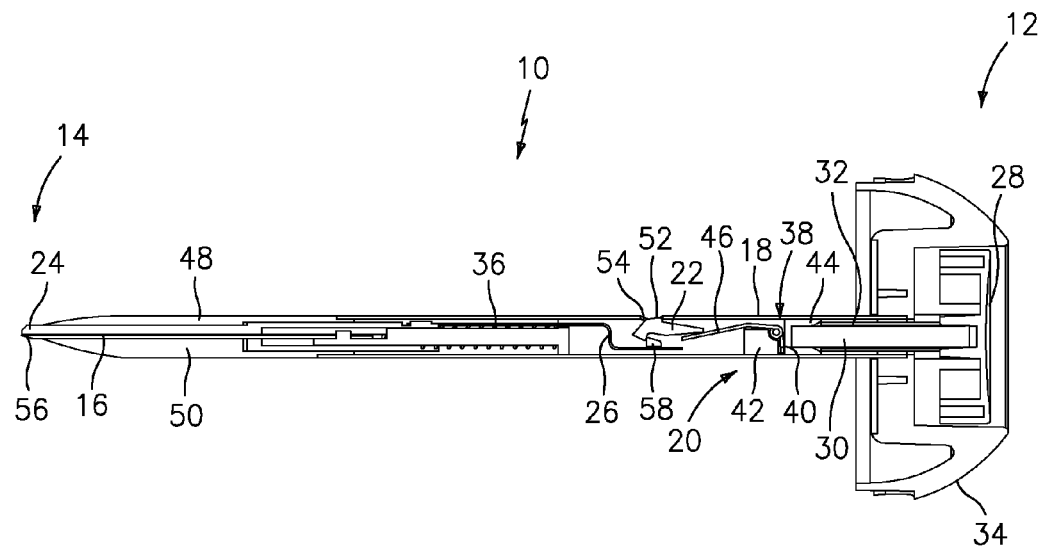
FIGS. 4 and 5 show a trocar in accordance with the present invention wherein the triggering assembly is being actuated.

FIG. 4 shows the trocar of the present invention in a triggering position wherein the blade and shield have both now penetrated the body wall, and thus shield 24 is pushed distally by spring 36. This distal movement of shield 24 positions shield 24 to again extend beyond the tip of blade 16 and causes lock release 26 to pivot lock 22 out of engagement with tube 18. This is done by the distal movement of tooth 58 which causes trigger 22 to pivot relative to blade holder 20 in a clockwise motion and thereby disengage catch member or ridge 52 from the hole in tube 18.

Figure 5:
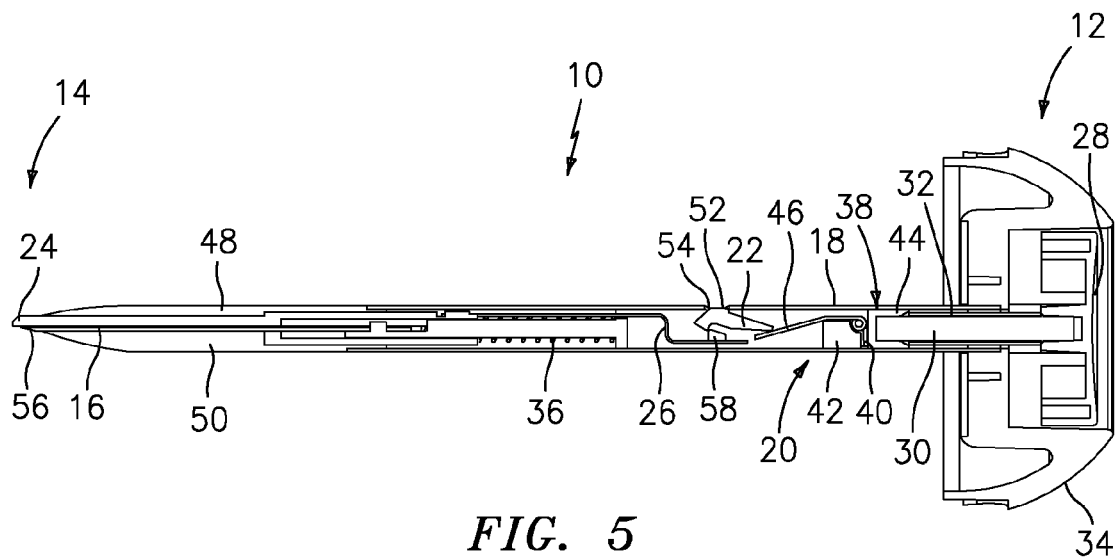

Turning to FIG. 5, this action of lock release member 26 and subsequent disengagement of lock member 22 from tube 18 results in a proximal movement of blade 16, blade holder 20 and blade lock member 22 driven by spring 36 so as to withdraw the sharp tip of blade 16 to within distal housing members 48, 50. It should be noted that when reference is made to the sharpened tip being "within" distal housing members 48, 50, what is meant is that the entire cutting edge of blade 16 is positioned at least coincident and preferably proximally of the extending blunt tip defined by distal housing members 48, 50.

From this position, it should be readily appreciated that absent depressing of button 28, blade 16 is secured within the structure and cannot inflict any unintended damage to tissues and the like.

As set forth above, trocar 10 in accordance with present invention further has a lancet function which advantageously allows for blade 16 to be used to make cutting incisions as may be desired, regardless of the shield member.

Figure 6:
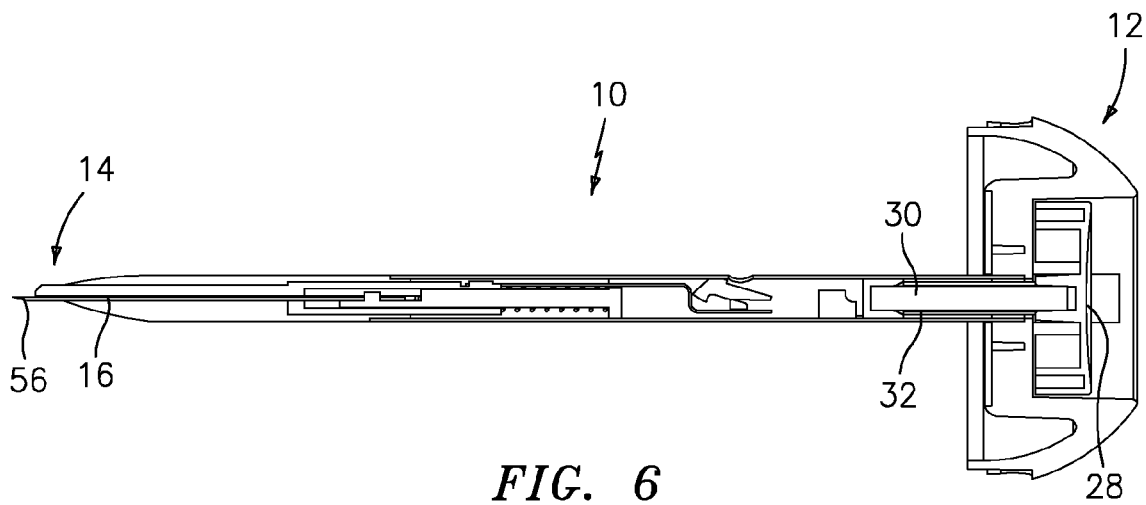
FIG. 6 shows a trocar in accordance with the present invention with the blade positioned in a lancet position.

FIG. 6 shows trocar 10 in this configuration, wherein a complete distal movement or depression of button 28 moves blade 16, blade holder 20 and blade lock member 22 distally past the armed position to a position where the sharp tip 56 of blade 16 extends beyond shield 24, even with shield 24 in the extended position. After the lancet function is completed, the trocar returns to the armed position as shown in FIG. 2, and can be used for subsequent procedures as desired.

Figure 7:
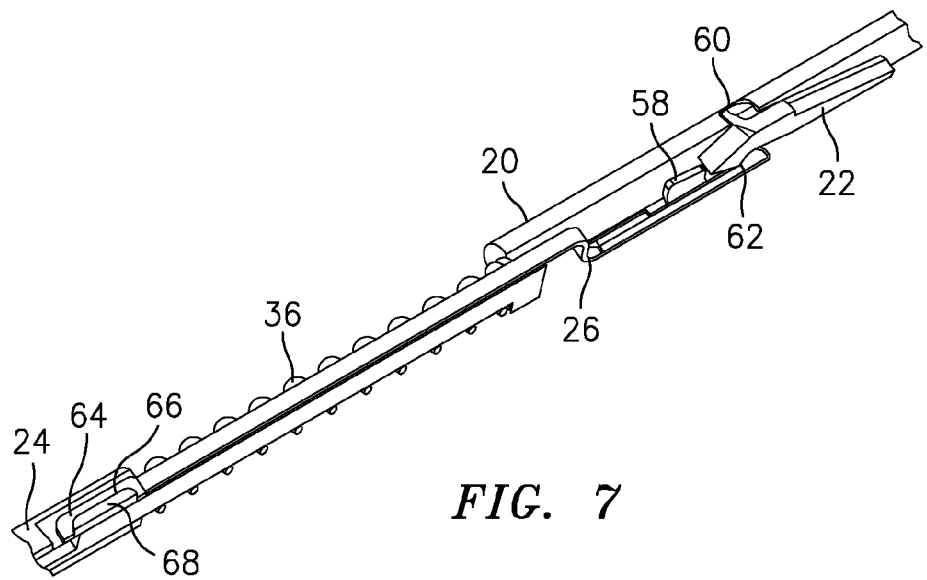
FIG. 7 illustrates an enlarged portion of the trocar of the present invention with the housing removed to illustrate functioning of the triggering assembly.

In accordance with the present invention, the blade lock 22 and lock release member 26 are shown in further detail in FIG. 7.

FIG. 7 shows these components of trocar 10 in an enlarged manner and with tube 18 removed. Thus, FIG. 7 shows blade holder 20 with blade lock member 22 pivotably mounted within a recess 60. This mounting defines a pivot point or axis of rotation of blade lock member 22 relative to blade holder 20 around the pivot point defined by recess 60.

Further as shown, lock release member 26 has tooth member 58 which is adapted to proximally slide past and catch a downwardly projecting ledge or surface 62 of blade lock member 22. To this end, tooth 58 can advantageously have a gradually sloping surface, which increases in height in a generally distal direction, and which thereby allows easy proximal movement of tooth 58 past surface 62 as desired.

FIG. 7 also shows the other end connection of lock release member 26 with shield 24, in this instance with a distal end 64 of lock release member 26 having an opening 66 into which a protruding post 68 of shield member 24 extends. In this way, shield 24 and lock release member 26 are axially mounted one relative to the other. Of course, shield 24 and lock release member 26 can be connected in other ways.

It should be appreciated that blade lock member 22 is shown in the drawings to be pivotably mounted relative to the blade assembly and pivotably mounted relative to the blade assembly and pivotable into engagement with housing 18. The reverse could also be true, with pivotable mounting of lock member 22 to housing 18 and pivot to engage the blade assembly.

It should also be noted that trigger/shield member 24 serves primarily as a trigger to cause retraction of the blade following an incision. In addition, the tip of trigger/shield 24 is relatively blunt and dull so as to serve a shielding function as well.

It should be readily appreciated that the trocar in accordance with the present invention advantageously provides for secure and safe positioning of the trocar through the body wall of a surgical patient while providing extraordinary protection to underlying tissues and organs from accidental or unintended injury during the procedure. Still further, the trocar in accordance with the present invention has an advantageous lancet function which provides additional useful employment of the trocar in accordance with the present invention.

The present description has been given as an exemplary embodiment of the present invention. It should readily be appreciated that these various components of the device can and would be provided from materials known to a person of skill in the art to be suitable for the intended purpose and to a suitable scale also for the intended purpose.

It should also be appreciated that various modifications of the parts and assembly of the present invention can be made and would still fall well within the scope of the present invention. Thus, the scope of the invention is defined by the amended claims, and the description given herein is in all respects to be treated as one example of the broad scope of the invention.

The invention claimed is:

1. A trocar assembly, comprising:
a trocar housing having a blunt distal end and a proximal end;
a blade assembly having a sharp tip and being slideable within the trocar housing between an armed position wherein the sharp tip extends distally beyond the blunt distal end and a relaxed position wherein the sharp tip is withdrawn proximally relative to the armed position wherein the blade assembly is substantially flat; and
a trigger member positioned relative to the housing to contact tissue when tissue is cut with the blade assembly in the armed position, and slideable by contact with the tissue to a proximal position which exposes the sharp tip and actuates a lock release member, the trigger member being substantially flat and mounted within the housing, and having a spring member biasing the trigger member distally so that removal of contact with the tissue allows the spring to move the trigger member distally, and further wherein distal movement of the trigger member with the lock release member activated releases the blade assembly from the armed position and allows the blade assembly to move to the relaxed position.

2. The assembly of claim 1, further comprising a blade lock member mounted to one of the blade assembly and the housing and releasably engageable with the other of the blade assembly and the housing whereby the blade assembly is releasably lockable in the armed position.

3. The assembly of claim 2, wherein the lock release member is selectively engaged by the blade lock member when the blade lock member is activated, and wherein movement of the lock release member when activated releases engagement of the blade lock member with the blade assembly or the housing.

4. The assembly of claim 2, wherein the blade lock member is pivotably mounted relative to one of the blade assembly and the housing and is pivotable between a locked position wherein the blade lock member engages the other of the blade assembly and the housing to prevent proximal movement of the blade assembly relative to the housing and an unlocked position wherein the blade assembly can move proximally from the armed position to the relaxed position.

5. The assembly of claim 4, wherein the blade lock member is pivotably mounted to the blade assembly and comprises a catch member for engaging the housing in the locked position, and a tooth for engaging with the lock release member.

6. The assembly of claim 5, further comprising a spring action on the blade lock member to urge the housing engaging surface into engagement with the housing.

7. The assembly of claim 6, wherein the blade lock member further comprises a first arm extending from the pivot point of the blade lock member relative to the blade assembly, and a second arm extending from the pivot point, and wherein the tooth is on the first arm and the spring acts on the second arm.

8. The assembly of claim 7, wherein the lock release member comprises a proximal facing surface for guiding the blade lock member during proximal movement of the lock release member relative to the blade lock member, and distal facing surface for engaging the blade lock member.

9. The assembly of claim 1, wherein the trigger member has a distal end and is slidable within the housing between an extended position wherein the distal end extends beyond the distal end of the housing and a triggered position wherein the distal end of the trigger member is positioned proximal of the distal end of the housing.

10. The assembly of claim 1, wherein the distal end of the housing is defined by two housing portions defining a slot therebetween, and wherein the blade assembly and the trigger member are slidable relative to the housing in the slot.

11. The assembly of claim 1, wherein the blade assembly is slidable relative to the housing to a lancet position wherein the sharp tip extends beyond the distal end of the housing and beyond a distal end of the trigger member.

12. The assembly of claim 1, wherein the spring member biases the trigger member to an extended position, and wherein the trigger member extends distally beyond the sharp tip of the blade assembly when the blade assembly is in the armed position and the trigger member is in the extended position.

* * * * *